(12) United States Patent
Zhao et al.

(10) Patent No.: US 11,518,740 B2
(45) Date of Patent: Dec. 6, 2022

(54) PLEUROMUTILIN (PHENYLTHIO)ACETIC ACID ESTER WITH ANTI-DRUG RESISTANT BACTERIA ACTIVITY AND A METHOD OF PREPARING THE SAME

(71) Applicants: Qianqian Zhao, Xi+3 an (CN); Jie Zhang, Xi+3 an (CN); Liang Xin, Xi+3 an (CN); Jingyi Li, Xi+3 an (CN); Ruina Bian, Xi+3 an (CN); Yuqing Zhao, Xi+3 an (CN); Dan Yang, Xi+3 an (CN); Han Li, Xi+3 an (CN); Bin Tian, Xi+3 an (CN); Yongbo Wang, Xi+3 an (CN); Chengyuan Liang, Xi+3 an (CN)

(72) Inventors: Qianqian Zhao, Xi+3 an (CN); Jie Zhang, Xi+3 an (CN); Liang Xin, Xi+3 an (CN); Jingyi Li, Xi+3 an (CN); Ruina Bian, Xi+3 an (CN); Yuqing Zhao, Xi+3 an (CN); Dan Yang, Xi+3 an (CN); Han Li, Xi+3 an (CN); Bin Tian, Xi+3 an (CN); Yongbo Wang, Xi+3 an (CN); Chengyuan Liang, Xi+3 an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 101 days.

(21) Appl. No.: 17/239,575

(22) Filed: Apr. 24, 2021

(65) Prior Publication Data
US 2022/0348539 A1   Nov. 3, 2022

(51) Int. Cl.
  *C07C 323/52* (2006.01)
  *C07C 319/20* (2006.01)

(52) U.S. Cl.
  CPC .......... *C07C 323/52* (2013.01); *C07C 319/20* (2013.01); *C07C 2603/82* (2017.05)

(58) Field of Classification Search
  None
  See application file for complete search history.

(56) References Cited

U.S. PATENT DOCUMENTS

| 3,979,423 A * | 9/1976 | Riedl ................... C07D 229/00 562/427 |
| 2003/0162831 A1* | 8/2003 | Ascher ................... A61P 31/00 514/529 |
| 2010/0184987 A1* | 7/2010 | Jaber ..................... C07C 303/28 560/147 |

FOREIGN PATENT DOCUMENTS

| CN | 109384698 | * | 2/2019 | ........... C07C 319/14 |
| CN | 111170893 | * | 5/2020 | ........... C07C 269/00 |

\* cited by examiner

*Primary Examiner* — Amy C Bonaparte

(57) ABSTRACT

A compound with anti-drug resistant bacteria activity having the following formula (I):

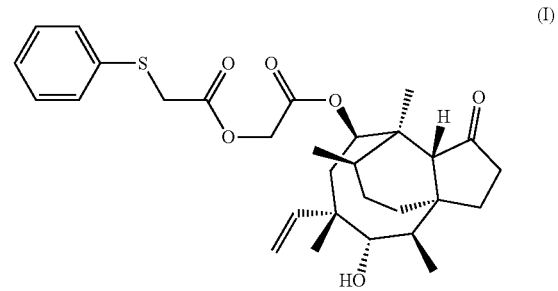

is disclosed. The methods of preparing the compound of formula (I) are also disclosed.

17 Claims, 2 Drawing Sheets

PLEUROMUTILIN (PHENYLTHIO)ACETIC ACID ESTER WITH ANTI-DRUG RESISTANT BACTERIA ACTIVITY AND A METHOD OF PREPARING THE SAME

FIELD OF THE INVENTION

The present invention relates to the field of medicinal chemistry, and in particular, to pleuromutilin (phenylithio) acetic acid ester with anti-drug resistant bacteria activity and a method of preparing the same.

BACKGROUND OF THE INVENTION

With the widespread use of antibiotics around the world, the overuse of antibiotics has become more and more common, and microorganisms that are resistant to the corresponding antibiotics have emerged, posing new threats to human health. Multidrug-resistant bacteria (MDROs) are bacteria that are resistant to three or more types of antibacterial drugs. In recent years, with the unreasonable use of antibiotics, pathogenic bacteria with multi-drug resistance have gradually emerged, posing a serious risk to public health. It is estimated that 10 million people in the world die each year due to bacterial resistance, and by 2050, bacterial resistance will cause 1 to 3.4 trillion U.S. dollars in economic losses worldwide each year. As people pay more attention to food safety and environmental protection, it will become a new direction for the research and development of new antibacterial drugs. The most common way to develop new drugs that can deal with multi-drug resistant bacteria is to modify the chemical structure of existing antibacterial drugs under the guidance of structure-activity relationship research.

Pleuromutilin (compound of formula II) is a tricyclic diterpenoid compound produced by the metabolism of *Pleurotus mutilus*. Using it as a precursor for structural modification has obtained Tiamulin, Valnemulin, and other highly active semi-synthetic antibiotics. Pleuromutilin and its derivatives can interfere with the binding of tRNA to the P-site and A-site by interacting with the peptide acyltransferase center of the bacterial ribosome, thereby inhibiting protein synthesis. Due to the special antibacterial mechanism and slow resistance of pleuromutilin and its derivatives, it has become one of the focus areas of current antibiotic research. Although pleuromutilin has good antibacterial activity, its bioavailability is low. Therefore, the design and synthesis of pleuromutilin derivatives with novel structure, strong antibacterial activity, good water solubility, and high bioavailability is of great significance for the treatment of multidrug-resistant bacterial infections.

(Phenylithio)acetic acid (CAS: 103-04-8) (compound of formula IV) is a pharmaceutical intermediate, which is a reactant for preparing benzoxazole, benzimidazole and benzothiazole with antibacterial activity.

The invention modifies pleuromutilin through (phenylithio)acetic acid structure to obtain a pleuromutilin (phenylithio)acetic acid ester. Preliminary antibacterial activity experiment shows the compound has excellent antibacterial activity and has high medical research and application value in the treatment of infectious diseases caused by multi-drug-resistant bacteria.

SUMMARY OF THE INVENTION

In one embodiment, the present invention provides a compound with anti-drug resistant bacteria activity having the following formula (I):

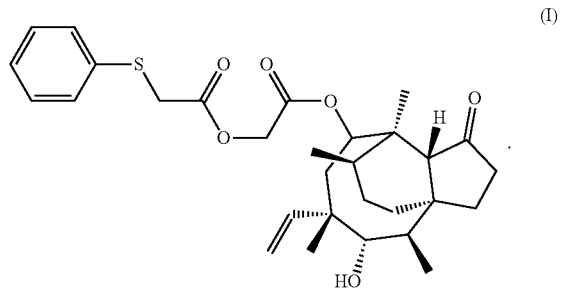 [SMILES: C=C[C@]1(C)CC(OC(=O)COC(=O)CSc2ccccc2)[C@]2(C)[C@H](C)CC[C@]3(CCC(=O)[C@H]32)[C@@H](C)[C@@H]1O]

In another embodiment, a method of preparing the compound of formula (I) includes: reacting a compound of formula (II) with a compound of formula (III) to obtain the compound of formula (I):

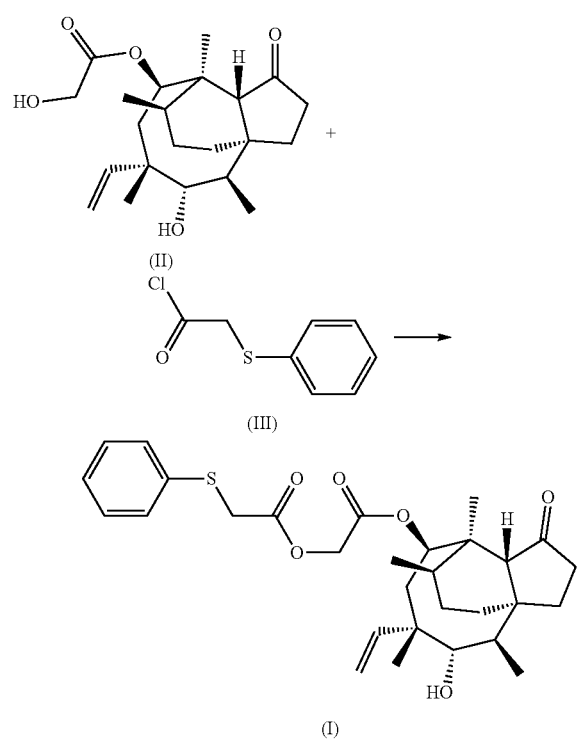

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalytic amount of triethylamine under nitrogen atmosphere to obtain a reaction mixture; heating the reaction mixture at 20-60° C. for 3-6 hours; extracting the reaction mixture with ethyl acetate to obtain a crude product; and purifying the crude product on a silica gel fresh chromatography column with petroleum ether and ethyl acetate as an eluent to obtain the compound of formula (I).

In another embodiment, the organic solvent is toluene, dichloromethane or N,N-dimethylformamide.

In another embodiment, the organic solvent is dichloromethane.

In another embodiment, the molar ratio of the compound of formula (II) and the compound of formula (III) is 1:1.1.

In another embodiment, the reaction mixture is heated at 25° C.

In another embodiment, the reaction mixture is heated for 5 hours.

In another embodiment, the eluent is petroleum ether: ethyl acetate=1:1.

In another embodiment, a method of preparing the compound of formula (I) includes: reacting a compound of formula (II) with a compound of formula (IV) to obtain the compound of formula (I):

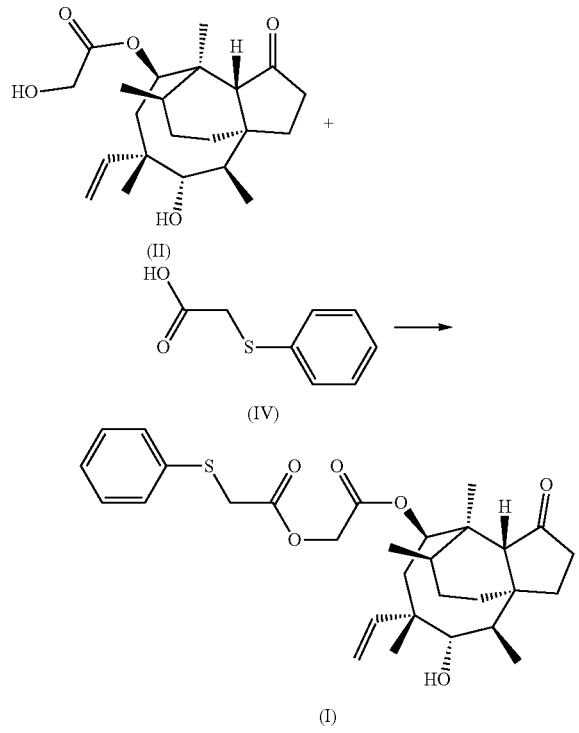

In another embodiment, the reaction of the compound of formula (II) with the compound of formula (IV) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (IV) to the reactor to form a reaction mixture; heating the reaction mixture at 20-50° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazolium hexafluorophosphate, 1-hexyl-3-methylimidazolium tetrafluoroborate, or 1-butyl-3-methylimidazolium tetrafluoroborate ([BMIM][BF$_4$]).

In another embodiment, the ionic liquid is the ionic liquid is 1-butyl-3-methylimidazolium tetrafluoroborate.

In another embodiment, the compound of formula (II) and the compound (IV) have a molar ratio of 1:1 to 1:1.3.

In another embodiment, the molar ratio of the compound of formula (II) and the compound of formula (IV) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
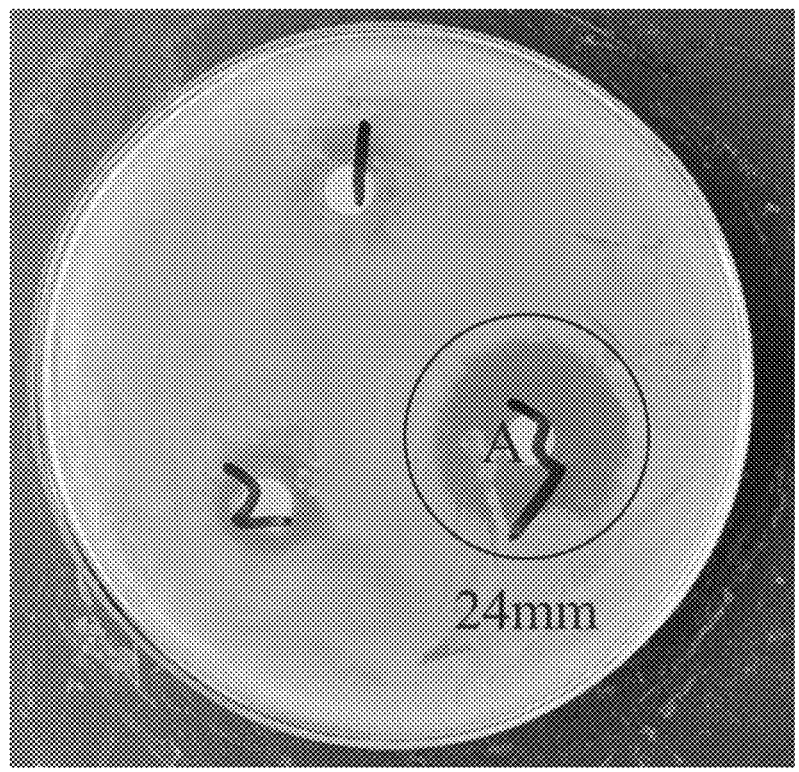
FIG. 1 shows the in vitro antibacterial activity of pleuromutilin (phenylithio)acetic acid ester against drug-resistant bacteria MRSA 18-171.

Reference will now be made in detail to embodiments of the present invention, example of which is illustrated in the accompanying drawings. The following examples illustrate the present invention, but the present invention is not limited to the following examples.

Example 1

Preparation of pleuromutilin (phenylithio)acetic acid ester (the compound of formula I) ((3aS,4R,5S,6S,8R,9R,9aR,12R)-5-hydroxy-4,6,9,12-tetramethyl-1-oxo-6-vinyl-decahydro-3a,9-propanocyclopenta[8]annulen-8-yl 2-(2-(phenylthio)acetoxy) acetate)

In a 100 mL three-necked flask, 246.0 mg (0.65 mmol) and 6.1 mg (0.06 mmol) triethylamine were dissolved in 15 mL of dichloromethane under nitrogen atmosphere. 134.4 mg (0.72 mmol) of (phenylithio)acetic acid chloride (compound of formula III) was dissolved in 10 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 246.2 mg of the title compound, a yield of 71.64%.

$^1$H-NMR (400 MHz, Chloroform-d) δ (ppm): 7.42 (3H, d), 6.45 (2H, d), 5.79 (1H, t), 5.23 (2H, d), 5.07 (2H, s), 4.54 (2H, t), 3.98(1H, t), 3.73 (1H, d), 3.35 (1H, d), 2.31 (1H, s), 2.20 (4H, t), 1.47-1.13 (11H, t), 1.13 (3H, t), 0.89 (3H, s), 0.72 (3H, s); $^{13}$C-NMR (100 MHz, Chloroform-d) δ (ppm): 216.7, 168.9, 166.1, 138.7, 134.7, 130.0, 129.0, 127.1, 117.3, 74.5, 70.6, 69.8, 61.9, 58.0, 44.7, 44.0, 41.4, 36.0, 26.8, 24.8, 16.7, 16.5, 14.7, 11.4.

Example 2

Preparation of pleuromutilin (phenylithio)acetic acid ester

In a 100 mL three-necked flask, 246.0 mg (0.65 mmol) and 6.1 mg (0.06 mmol) triethylamine were dissolved in 15 mL of N,N-dimethylformamide under nitrogen atmosphere. 134.4 mg (0.72 mmol) of (phenylithio)acetic acid chloride was dissolved in 10 mL of N,N-dimethylformamide, and added dropwise to the reaction mixture by a separatory funnel. After the completion of the dropwise addition, the reaction was carried out at 25° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether: ethyl acetate 2:1 as eluent, and the eluent was combined and concentrated under reduced pressure to obtain 220.4 mg of the title compound, a yield of 64.13%.

Example 3

Preparation of pleuromutilin (phenylithio)acetic acid ester

In a 100 mL three-necked flask, 246.0 mg (0.65 mmol) and 6.1 mg (0.06 mmol) triethylamine were dissolved in 15 mL of toluene under nitrogen atmosphere. 134.4 mg (0.72 mmol) of (phenylithio)acetic acid chloride was dissolved in 10 mL of toluene, and added dropwise to the reaction mixture by a separatory funnel. After the completion of the dropwise addition, the reaction was carried out at 30° C. for 6 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 223.63 mg of the title compound, a yield of 65.08%.

Example 4

Preparation of pleuromutilin (phenylithio)acetic acid ester

In a 100 mL three-necked flask, 246.0 mg (0.65 mmol) and 6.1 mg (0.06 mmol) triethylamine were dissolved in 15 mL of dichloromethane under nitrogen atmosphere. 145.6 mg (0.78 mmol) of (phenylithio)acetic acid chloride was dissolved in 10 mL of dichloromethane, and added dropwise to the reaction mixture by a separatory funnel. After the completion of the dropwise addition, the reaction was carried out at 20° C. for 6 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 230.7 mg of the title compound, a yield of 67.13%.

Example 5

Preparation of pleuromutilin (phenylithio)acetic acid ester

In a 100 mL three-necked flask, 246.0 mg (0.65 mmol) and 6.1 mg (0.06 mmol) triethylamine were dissolved in 15 mL of N,N-dimethylformamide under nitrogen atmosphere. 145.6 mg (0.78 mmol) of (phenylithio)acetic acid chloride was dissolved in 10 mL of N,N-dimethylformamide, and added dropwise to the reaction mixture by a separatory funnel. After the completion of the dropwise addition, the reaction was carried out at 40° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether: ethyl acetate 1:1 as eluent, and the eluent was combined and concentrated under reduced pressure to obtain 223.0 mg of the title compound, a yield of 64.89%.

Example 6

Preparation of pleuromutilin (phenylithio)acetic acid ester

In a 100 mL three-necked flask, 246.0 mg (0.65 mmol) and 6.1 mg (0.06 mmol) triethylamine were dissolved in 15 mL of dichloromethane under nitrogen atmosphere. 158.7 mg (0.85 mmol) of (phenylithio)acetic acid chloride was dissolved in 10 mL of dichloromethane, and added dropwise to the reaction mixture by a separatory funnel. After the completion of the dropwise addition, the reaction was carried out at 40° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 233.1 mg of the title compound, a yield of 67.83%.

Example 7

Preparation of pleuromutilin (phenylithio)acetic acid ester

In a 100 mL three-necked flask, 246.0 mg (0.65 mmol) and 6.1 mg (0.06 mmol) triethylamine were dissolved in 15 mL of toluene under nitrogen atmosphere. 134.4 mg (0.72 mmol) of (phenylithio)acetic acid chloride was dissolved in 10 mL of toluene, and added dropwise to the reaction mixture by a separatory funnel. After the completion of the dropwise addition, the reaction was carried out at 60° C. for 3 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 215.2 mg of the title compound, a yield of 62.62%.

Example 8

Preparation of pleuromutilin (phenylthio)acetic acid ester

In a 100 mL three-necked flask, 246.0 mg (0.65 mmol) and 6.1 mg (0.06 mmol) triethylamine were dissolved in 15 mL of dichloromethane under nitrogen atmosphere. 145.6 mg (0.7 8 mmol) of (phenylthio)acetic acid chloride was dissolved in 10 mL of dichloromethane, and added dropwise to the reaction mixture by a separatory funnel. After the completion of the dropwise addition, the reaction was carried out at 50° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 231.7 mg of the title compound, a yield of 67.42%.

Example 9

Preparation of pleuromutilin (phenylthio)acetic acid ester

In a 100 mL three-necked flask, 246.0 mg (0.65 mmol) and 6.1 mg (0.06 mmol) triethylamine were dissolved in 15 mL of toluene under nitrogen atmosphere. 145.6 mg (0.78 mmol) of (phenylthio)acetic acid chloride was dissolved in 10 mL of toluene, and added dropwise to the reaction mixture by a separatory funnel. After the completion of the dropwise addition, the reaction was carried out at 50° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 2:1 as eluent, and the eluent was combined and concentrated under reduced pressure to obtain 220.8 mg of the title compound, a yield of 64.25%.

Example 10

Preparation of pleuromutilin (phenylthio)acetic acid ester

In a 100 mL three-necked flask, 246.0 mg (0.65 mmol) and 6.1 mg (0.06 mmol) triethylamine were dissolved in 15 mL of toluene under nitrogen atmosphere. 121.3 mg (0.65 mmol) of (phenylthio)acetic acid chloride was dissolved in 10 mL of toluene, and added dropwise to the reaction mixture by a separatory funnel. After the completion of the dropwise addition, the reaction was carried out at 20° C. for 6 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 218.15 mg of the title compound, a yield of 63.48%.

Example 11

Preparation of pleuromutilin (phenylthio)acetic acid ester

In a 100 mL three-necked flask, 246.0 mg (0.65 mmol) and 6.1 mg (0.06 mmol) triethylamine were dissolved in 15 mL of dichloromethane under nitrogen atmosphere. 134.4 mg (0.72 mmol) of (phenylthio)acetic acid chloride was dissolved in 10 mL of dichloromethane, and added dropwise to the reaction mixture by a separatory funnel. After the completion of the dropwise addition, the reaction was carried out at 35° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 226.2 mg of the title compound, a yield of 65.82%.

Example 12

Preparation of pleuromutilin (phenylthio)acetic acid ester

In a 100 mL three-necked flask, 246.0 mg (0.65 mmol) and 6.1 mg (0.06 mmol) triethylamine were dissolved in 15 mL of dichloromethane under nitrogen atmosphere. 121.3 mg (0.65 mmol) of (phenylthio)acetic acid chloride was dissolved in 10 mL of dichloromethane, and added dropwise to the reaction mixture by a separatory funnel. After the completion of the dropwise addition, the reaction was carried out at 30° C. for 6 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 1:1 as eluent, and the eluent was combined and concentrated under reduced pressure to obtain 231.8 mg of the title compound, a yield of 67.45%.

Example 13

Preparation of pleuromutilin (phenylthio)acetic acid ester

In a 250 mL three-necked flask, 246.0 mg (0.65 mmol) of pleuromutilin, 121.1 mg (0.72 mmol) of (phenylthio)acetic acid and 12.0 mg (0.007 mmol) silicomolybdic acid were dissolved in 100 mL of 1-butyl-3-methylimidazolium tetrafluoroborate under nitrogen atmosphere. After full dissolution, the temperature of the reaction mixture was raised to 30° C. and the reaction was carried out for 6 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 297.5 mg of the title compound, a yield of 86.57%.

Example 14

Preparation of pleuromutilin (phenylithio)acetic acid ester

In a 250 mL three-necked flask, 246.0 mg (0.65 mmol) of pleuromutilin, 121.1 mg (0.72 mmol) of (phenylithio)acetic acid and 12.0 mg (0.007 mmol) silicomolybdic acid were dissolved in 100 mL of 1-butyl-3-methylimidazolium tetrafluoroborate under nitrogen atmosphere. After full dissolution, the temperature of the reaction mixture was raised to 20° C. and the reaction was carried out for 8 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 273.3 mg of the title compound, a yield of 79.53%.

Example 15

Preparation of pleuromutilin (phenylithio)acetic acid ester

In a 250 mL three-necked flask, 246.0 mg (0.65 mmol) of pleuromutilin, 121.1 mg (0.72 mmol) of (phenylithio)acetic acid and 12.0 mg (0.007 mmol) silicomolybdic acid were dissolved in 100 mL of 1-octyl-3-methylimidazolium hexafluorophosphate under nitrogen atmosphere. After full dissolution, the temperature of the reaction mixture was raised to 40° C. and the reaction was carried out for 6 hours. Thin layer chromatography was used to track the reaction to completion, heating was stopped, and the protective device was removed. The reaction mixture system was allowed to separate into layers to give a crude product. 1-Octyl-3-methylimidazolium hexafluorophosphate was recovered. The crude product was recrystallized with 30 mL methanol and dried to obtain 266.3 mg of the title compound, a yield of 77.49%.

Example 16

Preparation of pleuromutilin (phenylithio)acetic acid ester

In a 250 mL three-necked flask, 246.0 mg (0.65 mmol) of pleuromutilin, 121.1 mg (0.72 mmol) of (phenylithio)acetic acid and 12.0 mg (0.007 mmol) silicomolybdic acid were dissolved in 100 mL of 1-hexyl-3-methylimidazolium tetrafluoroborate under nitrogen atmosphere. After full dissolution, the temperature of the reaction mixture was raised to 40° C. and the reaction was carried out for 6 hours. Thin layer chromatography was used to track the reaction to completion, heating was stopped, and the protective device was removed. The reaction mixture system was allowed to separate into layers to give a crude product. 1-Hexyl-3-methylimidazolium tetrafluoroborate was recovered. The crude product was recrystallized with 30 mL methanol and dried to obtain 257.8 mg of the title compound, a yield of 75.02%.

Example 17

Antibacterial Activity Test of the Compounds of the Invention

The antimicrobial efficacy was determined by a paper diffusion method drug sensitivity test.

Experimental strains: multi-resistant *Staphylococcus aureus* 171, multi-resistant *Staphylococcus aureus* 222, multi-resistant *Staphylococcus aureus* 596. The experimental strains were identified by Huashan Hospital Affiliated to Fudan University (Institute of Antibiotic of Fudan University).

Drug sensitive paper: The drug sensitive paper is a special drug sensitive paper with a diameter of 6.35 mm and a water absorption of 0.02 mL. The control drug was vancomycin (30 μg/tablet); the test drugs were pleuromutilin (phenylithio)acetic acid ester (30 μg/tablet).

Reagents: LB agar medium, LA broth medium, dichloromethane.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. Pick a single colony that grows well and inoculate it into broth medium, incubate at 35° C.±2° C. for 6 hours, and use LA broth medium to calibrate the concentration of the bacterial solution to 0.5 Mie turbidimetric tube ($1.5 \times 10^8$ CFU/mL). A bacterial suspension is obtained.

The experimental strains were inoculated in non-selective medium and placed in air at 37° C. for 24 h. Pick a single colony that grows well and inoculate it into broth medium, incubate at 35° C.±2° C. for 6 hours, and use LA broth medium to calibrate the concentration of the bacterial solution to 0.5 Mie turbidimetric tube ($1.5 \times 15^8$ CFU/mL). A bacterial suspension is obtained.

Paper Diffusion Method Drug Sensitivity Test:

LB dry powder was weighed, sterilized at 103.4 Kpa, 121.3° C. high-pressure steam for 15 min, and then placed it in a 40° C.-50° C. water bath. A sterile empty plate (inner diameter 9 cm) was placed on the surface of the ultra-clean table water table, and LB dry powder was poured to the plate. The thickness of each plate was 3 mm to 4 mm. After the plate was cooled at room temperature, it was stored in the refrigerator at 2° C.-8° C. A sterile cotton swab was used to dip the bacterial solution and to evenly coat the surface of the LB plate 3 times. After inoculation of the bacterial suspension, the LB plate was dried at room temperature for 3 min to 5 min. Sterile forceps were used to closely attach the antibacterial drug paper to the dish. The dish was put upside down and placed in a 37° C. incubator for 24 h. The results were observed by measuring the diameter. Taking 0.5% DMSO solution as a negative control, the antibacterial activity is expressed by the diameter of the inhibition zone. The inhibition zone≥17 mm, sensitive; the inhibition zone of 15 mm-16 mm, intermediary; the inhibition zone≤14 mm, drug resistance.

Figure 2:
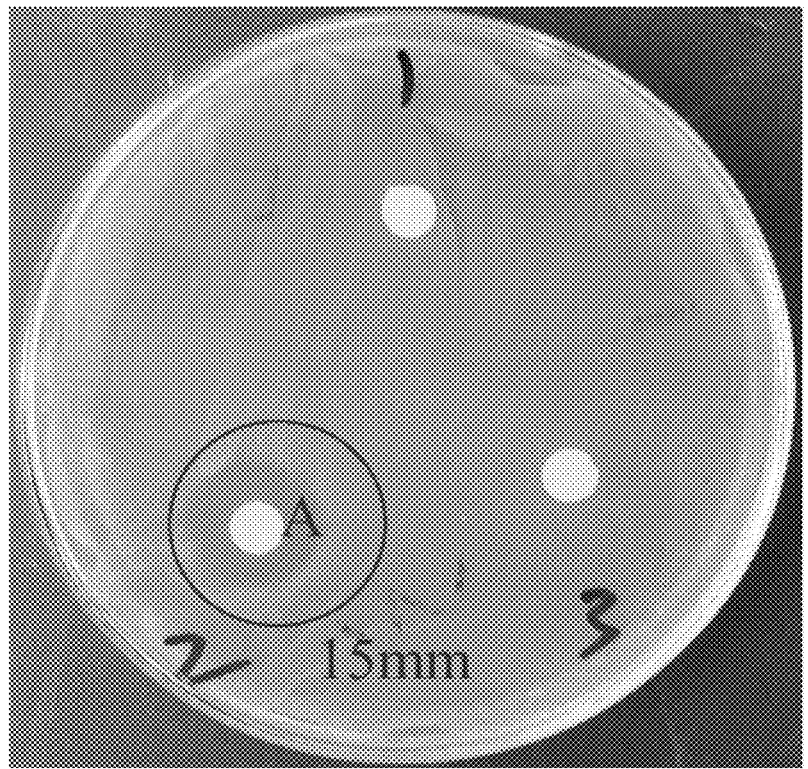
FIG. 2 shows the in vitro antibacterial activity of pleuromutilin (phenylithio)acetic acid ester against drug-resistant bacteria MRSA 18-222.
Figure 3:
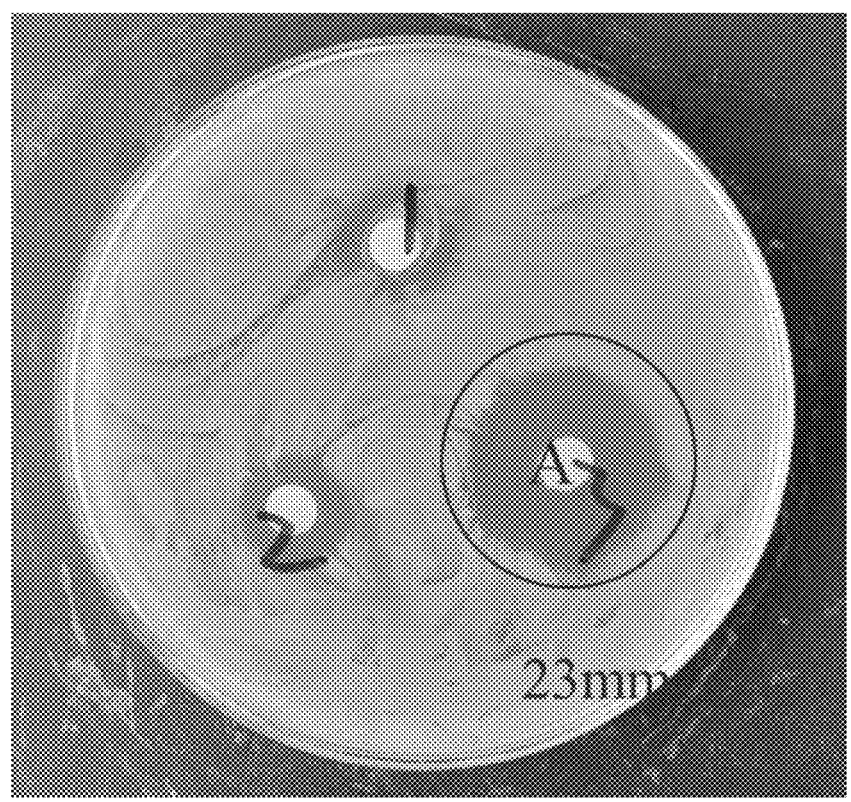
FIG. 3 shows the in vitro antibacterial activity of pleuromutilin pleuromutilin (phenylithio)acetic acid ester against drug-resistant bacteria MRSA 18-596.

In FIGS. 1-3, pleuromutilin (phenylithio)acetic acid ester is represented by the letter A. FIG. 1 shows the antibacterial effect of pleuromutilin (phenylithio)acetic acid ester on MRSA-171. FIG. 2 shows the antibacterial effect of pleuromutilin (phenylithio)acetic acid ester on MRSA-222. FIG.

3 shows the antibacterial effect of pleuromutilin (phenylithio)acetic acid ester on MRSA-596. The results are also shown in Table 1.

TABLE 1

Experimental results of the zone of inhibition

| Compound | Zone of inhibition /mm Strain | | |
|---|---|---|---|
|  | MRSA-171 | MRSA-222 | MRSA-596 |
| Vancomycin | 17 | 18 | 21 |
| Pleuromutilin | 0 | 0 | 0 |
| (Phenylithio)acetic acid | 0 | 0 | 0 |
| Pleuromutilin (phenylithio)acetic acid ester | 24 | 15 | 23 |

The results in FIGS. 1-3 and Table 1 show that pleuromutilin and (phenylithio)acetic acid have no inhibitory effect on drug-resistant bacteria. Pleuromutilin (phenylithio)acetic acid ester has strong inhibitory effects on multi-drug resistant *Staphylococcus aureus* 171, 222, 596, and the diameter of bacteriostatic zone against multidrug resistant *Staphylococcus aureus* 171 was up to 24 mm. In summary, the pleuromutilin (phenylithio)acetic acid ester of the present invention can be used as an antibacterial drug candidate for multi-drug resistant *Staphylococcus aureus*, and further preclinical studies will be conducted.

What is claimed is:

1. A compound with antibacterial activity against drug resistant bacteria having the following formula (I):

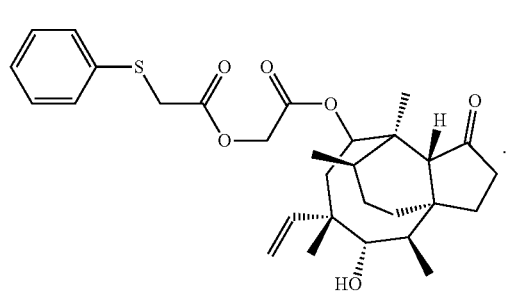

(I)

2. A method of preparing the compound of formula (I) of claim 1, comprising:
   reacting a compound of formula (II) with a compound of formula (III) to obtain the compound of formula (I):

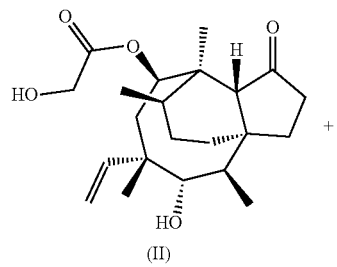

(II)

+

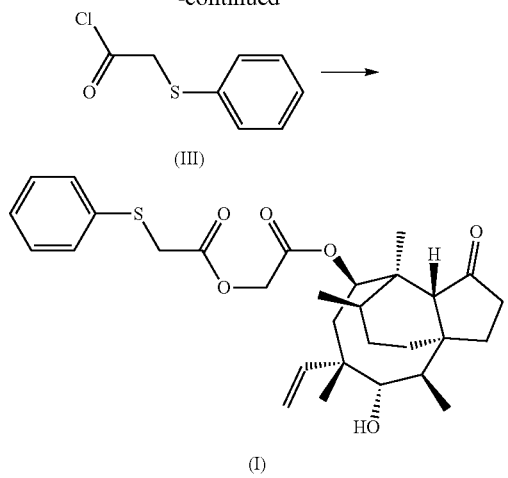

3. The method of claim 2, wherein the reaction of the compound of formula (II) with the compound of formula (III) comprises the following steps:
   placing the compound of formula (II) and the compound of formula (III), in a molar ratio of 1:1 to 1:1.3, in a reactor;
   adding an organic solvent and a catalytic amount of triethylamine under a nitrogen atmosphere to obtain a reaction mixture;
   heating the reaction mixture at 20-60° C. for 3-6 hours;
   extracting the reaction mixture with ethyl acetate to obtain a crude product; and
   purifying the crude product on a silica gel chromatography column with petroleum ether and ethyl acetate as an eluent to obtain the compound of formula (I).

4. The method of claim 3, wherein the organic solvent is toluene, dichloromethane or N,N-dimethylformamide.

5. The method of claim 4, wherein the organic solvent is dichloromethane.

6. The method of claim 3, wherein the molar ratio of the compound of formula (II) and the compound of formula (III) is 1:1.1.

7. The method of claim 3, wherein the reaction mixture is heated at 25° C.

8. The method of claim 3, wherein the reaction mixture is heated for 5 hours.

9. The method of claim 3, wherein the eluent is petroleum ether:ethyl acetate=1:1.

10. A method of preparing the compound of formula (I) of claim 1, comprising:
    reacting a compound of formula (II) with a compound of formula (IV) to obtain the compound of formula (I):

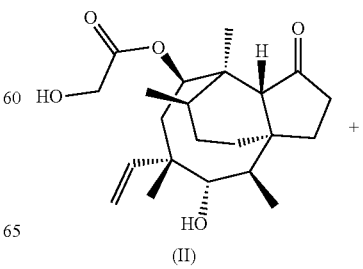

(II)

+

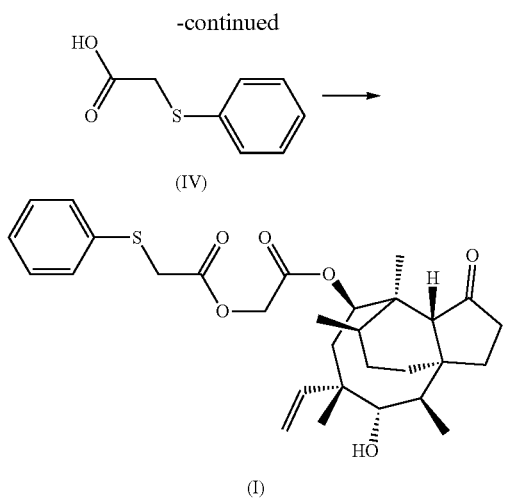

11. The method of claim 10, wherein the reaction of the compound of formula (II) with the compound of formula (IV) comprises the following steps:
placing the compound of formula (II), a catalyst, and an ionic liquid in a reactor under nitrogen atmosphere, the catalyst being 12-molybdosilicic acid hydrate of formula $H_6Mo_{12}O_{41}Si$;
adding the compound of formula (IV) to the reactor to form a reaction mixture;
heating the reaction mixture at 20-50° C. for 4-8 hours;
placing the reaction mixture in a separating funnel to separate a crude product;
purifying the crude product by recrystallization in methanol to obtain the compound of formula (I); and
recycling the ionic liquid.

12. The method of claim 11, wherein the ionic liquid is 1-octyl-3-methylimidazolium hexafluorophosphate, 1-hexyl-3-methylimidazolium tetrafluoroborate, or 1-butyl-3-methylimidazolium tetrafluoroborate ([BMIM][BF$_4$]).

13. The method of claim 12, wherein the ionic liquid is 1-butyl-3-methylimidazolium tetrafluoroborate.

14. The method of claim 11, wherein the compound of formula (II) and the compound (IV) have a molar ratio of 1:1 to 1:1.3.

15. The method of claim 14, wherein the molar ratio of the compound of formula (II) and the compound of formula (IV) is 1:1.1.

16. The method of claim 11, wherein the reaction mixture is heated at 30° C.

17. The method of claim 11, wherein the reaction mixture is heated for 6 hours.

* * * * *